(12) United States Patent
Wikefeldt

(10) Patent No.: US 6,523,538 B1
(45) Date of Patent: Feb. 25, 2003

(54) BREATHING CIRCUIT HAVING IMPROVED WATER VAPOR REMOVAL

(75) Inventor: Per Wikefeldt, Jarfalla (SE)

(73) Assignee: Instrumentarium Corp., Helsinki (FI)

( * ) Notice: Subject to any disclaimer, the term of this patent is extended or adjusted under 35 U.S.C. 154(b) by 0 days.

(21) Appl. No.: 09/478,169

(22) Filed: Jan. 5, 2000

(51) Int. Cl.[7] ............................................. A61M 16/00
(52) U.S. Cl. ............................. 128/204.18; 128/205.12
(58) Field of Search ...................... 128/204.18, 204.21, 128/204.22, 204.23, 205.12–205.15, 204.14, 204.15, 204.16, 204.17, 205.28, 911, 912

(56) References Cited

U.S. PATENT DOCUMENTS

| | | | |
|---|---|---|---|
| 3,575,167 A | * 4/1971 | Michielsen | 128/200.24 |
| 3,659,590 A | * 5/1972 | Jones et al. | 600/538 |
| 4,314,566 A | 2/1982 | Kiwak | |
| 4,509,359 A | 4/1985 | Gedeon et al. | |
| 4,516,573 A | 5/1985 | Gedeon | |
| 4,993,230 A | * 2/1991 | Hingst | 67/512 |
| 5,479,923 A | 1/1996 | Rantala | |
| 5,664,563 A | * 9/1997 | Schroeder et al. | 128/204.25 |
| 5,678,540 A | * 10/1997 | Kock et al. | 128/205.13 |
| 5,722,393 A | 3/1998 | Bartel et al. | |
| 5,829,428 A | * 11/1998 | Walters et al. | 128/200.24 |
| 6,131,571 A | * 10/2000 | Lampotang et al. | 128/204.21 |
| 6,134,462 A | 10/2000 | Rantala | |
| 6,152,131 A | * 11/2000 | Heinonen | 128/204.23 |
| 6,220,245 B1 | * 4/2001 | Takabayashi et al. | 128/202.12 |

FOREIGN PATENT DOCUMENTS

| | | |
|---|---|---|
| DE | 41 11 138 | 10/1992 |
| EP | 535 379 | 4/1993 |
| FR | 2315955 | 1/1977 |
| GB | 2053695 | 2/1981 |
| GB | 2139110 | 11/1984 |
| GB | 2224957 | 5/1990 |
| WO | 99/27988 | 6/1999 |

\* cited by examiner

*Primary Examiner*—John G. Weiss
*Assistant Examiner*—Teena K Mitchell
(74) *Attorney, Agent, or Firm*—Andrus, Sceales, Starke & Sawall, LLP

(57) ABSTRACT

A breathing circuit of the closed circuit type has improved means for removing water vapor to prevent condensation within the circuit. A dryer is placed in the breathing circuit, downstream of the $CO_2$ absorber, for removing water vapor from the breathing gases, including that entrained in the breathing gases during passage through the $CO_2$ absorber. The dryer may utilize a thermoelectric cooling element or a water vapor permeable membrane.

21 Claims, 4 Drawing Sheets

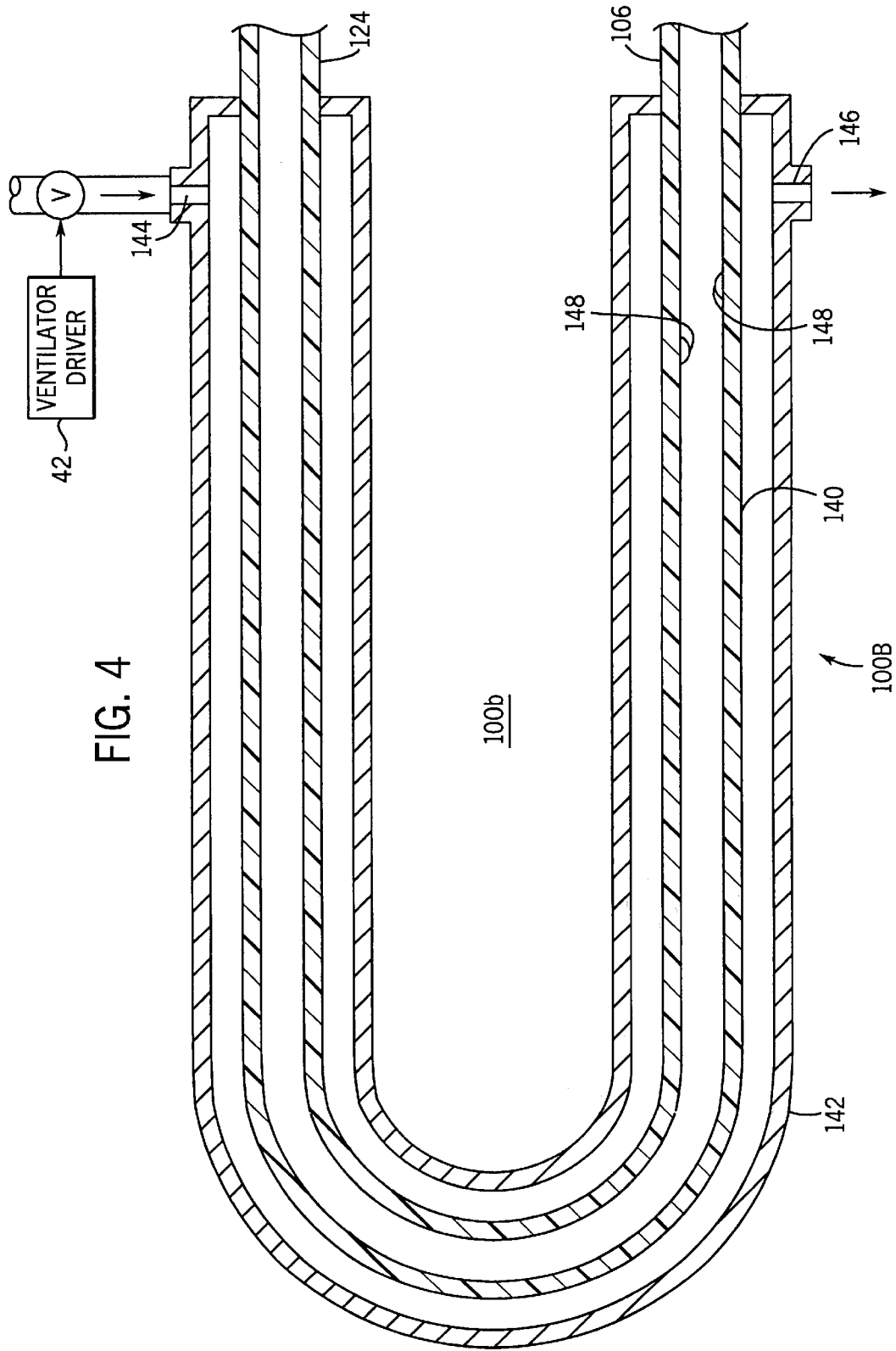

BREATHING CIRCUIT HAVING IMPROVED WATER VAPOR REMOVAL

BACKGROUND OF THE INVENTION

The present invention relates to a breathing circuit having an improved means for removing water vapor from the circuit. Condensation of the water vapor within the breathing circuit, and its attendant problems, is thus lessened or eliminated. The invention is particularly suited for use in breathing circuits characterized as being of the closed type.

During breathing, a volume of breathing gas, termed the tidal volume, is inhaled into the lungs during inspiration and exhaled during expiration. Tidal volumes typically range from 400–1000 milliliters (ml), depending on the size of the subject's lungs. When in the lungs, the breathing gases become moistened and water vapor is discharged with the breathing gases when they are expired. About 35 milligrams (mg) of water are discharged by a person with each breath, assuming a tidal volume of about 1000 milliliters.

A mechanical ventilator may be used to supply and remove breathing gases to/from the subject. This may be done to assist or replace the natural breathing action of the subject, in connection with the supply of an anaesthetic agent to the subject, or for other reasons. A typical mechanical ventilator has an inspiration limb for supplying breathing gases to the subject and an expiration limb for receiving breathing gases from the subject. The inspiration and expiration limbs are each connected to arms of a Y-connector. A patient limb extends from a third arm of the Y-connector to an intubation tube or face mask for the subject.

A common type of mechanical ventilator recirculates the expired breathing gases of the subject in the expiration limb through a $CO_2$ absorber back to the inspiration limb for rebreating by the subject. Such a closed breathing circuit prevents loss of anaesthetic agents to the ambient air. Such breathing circuits are often operated in a "low flow" mode in which, at least in principle, the amount of fresh, dry breathing gases added to the breathing circuit is only that necessary to replace the gases consumed by the subject.

However, the $CO_2$ absorber in such a circuit acts as a moisture reservoir so that additional moisture, for example, an additional 15 mg of water per breath becomes entrained in the breathing gases circulating in the closed breathing circuit.

While it is preferable that the subject breath moist, warm breathing gases, the presence of such gases in the breathing circuit does have disadvantages. When the warm, moist breathing gases expired by the subject, which are at body temperature, pass through the breathing circuit, which is at room temperature, the water vapor in the breathing gases condenses on components of the breathing circuit. As the breathing of the subject continues, the condensed water accumulates. The accumulated water may interfere with the operation of valves, sensors, or other components of the breathing circuit or form a medium for microbiological growth within the circuit. Such accumulations therefore present a problem in closed circuit breathing systems.

Various solutions have been proposed to remedy this problem. Water traps may be inserted in the breathing circuit in an effort to prevent water from reaching critical components. Or, all, or the portions, of the breathing circuit particularly effected by moisture accumulation, may be heated to prevent condensation of the water vapor. This may be carried out for example by resistance heaters, such as wires that are wrapped around the tubing of the limbs, and around valves, etc.

However, while heating can delay the onset of condensation and prevent condensation in critical parts of the circuit, it is difficult or impossible to fully prevent precipitation of water vapor out of the breathing gases.

Many breathing circuits incorporate a humidity and moisture exchanger (HME) in the patient limb in which heat and moisture from exhaled breathing gases are exchanged to the breathing gases to be inhaled by the subject. The primary purpose of such an exchanger is to provide for patient comfort by preheating the inhaled breathing gases and to ensure that the patient does not inhale dry breathing gas. However, in the usual case, not all moisture in the exhaled breathing gases is transferred to the inhaled breathing gases. A small amount, which can be characterized as "leakage" remains in the exhaled gases and circulates in the breathing circuit. Thus, the reduction in the moisture level of the exhaled gases entering the breathing circuit, as a result of humidifying the inhaled gases, may also delay, but usually will not fully prevent, condensation and moisture accumulation in other portions of the breathing circuit.

Due to the additional amount of water inserted in the breathing gases by the $CO_2$ absorber, the amount of breathing gas water vapor is increased in the portions of the breathing circuit between the absorber and the subject, exacerbating the problems of moisture condensation on sensors, traps, and the like in this portion of the circuit.

The problem is particularly acute when a ventilator is operated in a low-flow manner since the breathing gases are continually recirculating and little fresh, dry gas is being added.

BRIEF SUMMARY OF THE INVENTION

The present invention is thus directed to a breathing circuit having an improved means for removing water vapor from the breathing gases in the breathing circuit. Condensation within the breathing circuit and its attendant problems is thereby lessened or eliminated, including that occurring under low flow conditions.

Briefly, the breathing circuit of the present invention incorporates a dryer downstream of the $CO_2$ absorber for removing water vapor from the breathing gases. The dryer may incorporate means, such as a thermoelectric element, for cooling breathing gases passing through the absorber so that the water vapor condenses out of the breathing gases. A fan may be used in conjunction with the thermoelectric element to improve its performance. The dryer may include a heat transfer means for reheating the cooled, drier breathing gases with incoming gases from the $CO_2$ absorber.

Or, the breathing gases may be passed along a water permeable membrane such as a water permeable tube to remove the water vapor from the breathing gases. The tube may be jacketed so that dry air can be supplied to the other side of the tube to improve the removal of the water vapor.

BRIEF DESCRIPTION OF THE SEVERAL VIEWS OF THE DRAWING

Various other features, objects, and advantages of the invention will be made apparent from the following detailed description and the drawings in which:

FIG. 4 is a schematic, cross sectional view of an alternative embodiment of a dryer suitable for incorporation in a breathing circuit of the present invention.

DETAILED DESCRIPTION OF THE INVENTION

Figure 1:
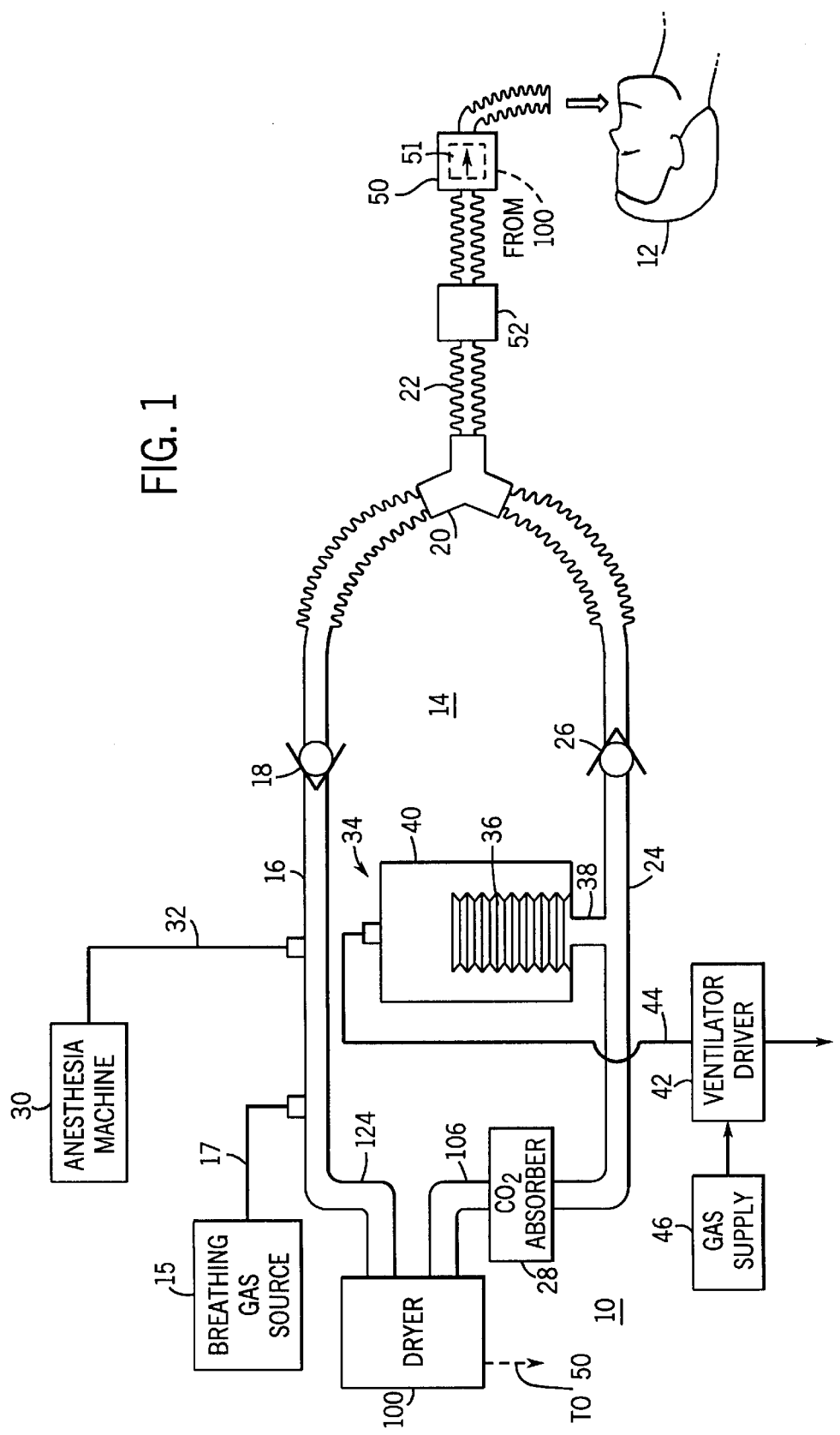
FIG. 1 is a general, somewhat schematic view of a breathing circuit of the present invention.

FIG. 1 shows a ventilation system 10 for mechanically ventilating subject 12. Ventilation system 10 includes closed breathing circuit 14 which can be charged with breathing gases from source 15 via conduit 17. Breathing circuit 14 has inspiration limb 16 having inspiration check valve 18. Inspiration limb 16 is connected to the inlet of Y-piece connector 20. Patient limb 22, also connected to Y-connector 20, supplies breathing gases to subject 12 during inspiration and receives breathing gases from the subject during expiration.

Expiration limb 24 is connected to the output of Y-connector 20 to receive the exhaled breathed gases and includes expiration check valve 26. Expiration limb 24 is connected to the inlet of carbon dioxide ($CO_2$) absorber 28, the outlet of which is customarily connected to inspiration limb 16 to complete the closed breathing circuit. $CO_2$ absorber 28 may contain soda lime or other suitable $CO_2$ absorbent. Anaesthesia machine 30 may be connected to inspiration limb 16 via conduit 32 to supply and maintain an anaesthetic agent in the breathing gases in circuit 14. Various flow sensors and pressure sensors, not shown, may also be connected in the breathing circuit.

Bellows assembly 34 is used to separate the breathing gases in breathing circuit 14 from driving gases that supply the energy necessary to provide the breathing gases to subject 12 during inspiration. Bellows assembly 34 includes expandable, pleated bellows 36. Bellows 36 is connected to expiration limb 24 by pipe 38. Bellows 36 is contained in housing 40. In a typical ventilation system, bellows 36 expands upwardly and contracts downwardly in housing 40.

Bellows assembly 34 is operated by ventilator driver 42 which is coupled to housing 40 by supply line 44. Driver 42 is connected to a driving gas supply 46. Ventilation driver 42 includes a gas flow control valve which may be operated by a waveform generator that provides desired gas flow in supply line 44. Gas so supplied to housing 40 compresses bellows 36 downwardly, forcing the breathing gases in the bellows and in the downstream portions of breathing circuit 14 through $CO_2$ absorber 28, inspiration limb 16, Y-piece connector 20, and patient limb 22 to subject 12. As noted above, water retained in $CO_2$ absorber 28 is entrained in the breathing gases as they pass through $CO_2$ absorber 28. The volume of breathing gases delivered to subject 12 is determined by the amount of driving gas supplied to housing 40.

During expiration, the driving gas in housing 40 is allowed to exit the housing, permitting bellows 36 to expand upwardly and receive the exhaled gases as subject 12 breaths out. The exhaled gases are provided to bellows 36 via expiration limb 24 and expiration check valve 26.

On the next breath for subject 12, bellows 36 is again compressed by the driving gas to provide breathing gases to the subject. The $CO_2$ in the breathing gases previously exhaled by the subject is removed by $CO_2$ absorber 28 and the breathing gases pass through inspiration limb 16 for delivery to subject 12. The breathing gases subsequently exhaled by the subject are again received in expiration limb 24 and bellows 36.

Breathing circuit may include various sensors, such as flow sensors qualitative gas sensors, and pressure sensors, that monitor the operation of the breathing circuit. Conventionally, the breathing circuit may also contain water traps (not shown) at locations, such as at sensors, known to collect water. Patient limb 22 will typically include breathing gas sampling tubes for the sensors, a bacterial filter, and other elements, collectively shown as 52.

Patient limb 22 also includes humidity and moisture exchanger (HME) 50 for exchanging heat and moisture from the exhaled breathing gases to the inhaled breathing gases. To this end, heat and moisture exchanger 50 may include a porous element 51 impregnated with a hygroscopic agent.

In accordance with the present invention, and as shown in FIG. 1, dryer 100 is inserted in breathing circuit 14, downstream of $CO_2$ absorber 28 for removing moisture from the breathing gases circulating in the breathing circuit. In the embodiment shown in FIG. 2, dryer 100 has housing 102 formed of plastic or other suitable material. An inlet connector 104 receives conduit 106 leading from $CO_2$ absorber 28 for receiving warm, moist, exhaled breathing gases which have been scrubbed of $CO_2$ in the absorber. The air passes through a first chamber 108 of housing 102 in conduit 109 to second chamber 110. Second chamber 110 contains thermoelectric element 112 which may be a Peltier or similar element. In such an element, a current through the element creates a cold surface of the element and a warm surface of the element. In dryer 100, element 112 is arranged so that the cold surface 112a is exposed in second chamber 110. One or both surfaces of thermoelectric element 112 may be finned to improve heat transfer. If desired, a fan 114 may move air from vents 116 across the warm surface 112b of thermoelectric element 112 to remove heat from that surface to further improve the performance of the thermoelectric element. Element 112 and fan 114 may be provided with electric current in conductors 118, respectively. Thermoelectric element 112 may be provided with a temperature sensor for control or safety purposes.

The warm, moist breathing gases from conduit 106 pass over the cold surface of thermoelectric element 112 and are cooled, condensing water vapor out of the breathing gases. The condensed water can be removed from chamber 110 at drain 120.

The breathing gases then pass from second chamber 110 back through first chamber 108 in conduit 113 and to connector 122 for conduit 124. Conduit 124 returns the dried breathing gases to the breathing circuit. In the return passage through first chamber 108 in conduit 113, the breathing gases are reheated by incoming breathing gases from conduit 109. Heat exchange fins 111 and 115 may be provided on conduits 109 and 113, respectively, to improve the heat transfer. Re-heating the air discharged from dryer 100 assists in providing comfort to subject 12 as the breathing gases are respired while providing a measure of cooling to the breathing gases being supplied to dryer 100 in chamber 110. If further reheating of the breathing gases is desired, the discharge from fan 114 may be provided to heat exchanger 126 to transfer the heat drawn off thermoelectric element 112 to the breathing gases in conduit 124, as shown schematically in FIG. 2A.

In some cases, it may be possible to eliminate thermoelectric element 112 and employ the heat exchange between the outgoing and incoming breathing gases to cool the latter to remove moisture.

Figure 2:
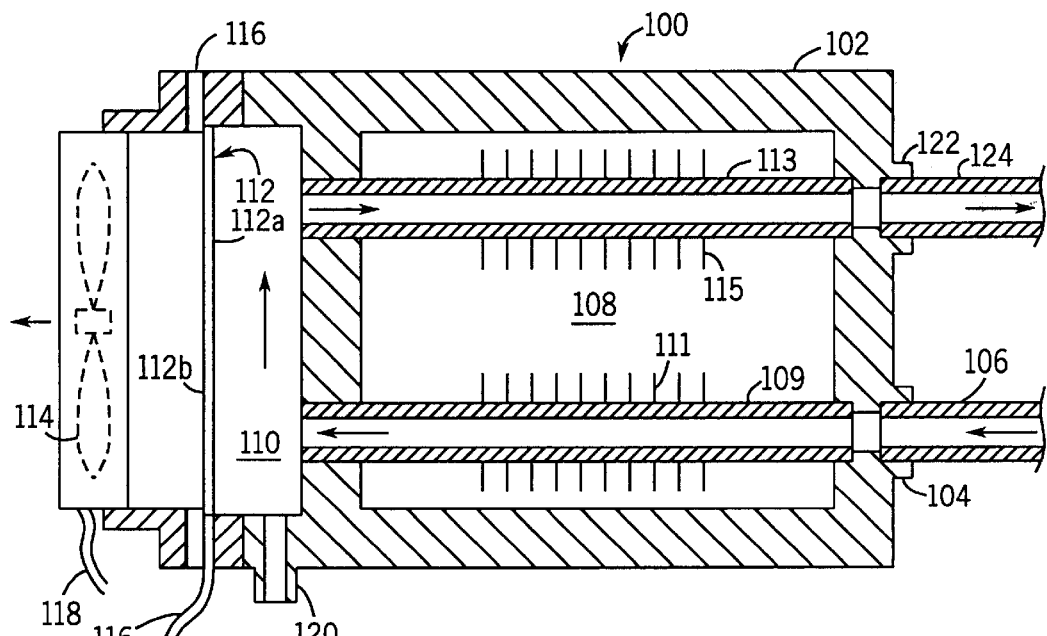
FIG. 2 is a schematic, cross sectional view of a dryer incorporated in the breathing circuit of the present invention.
Figure 2A:
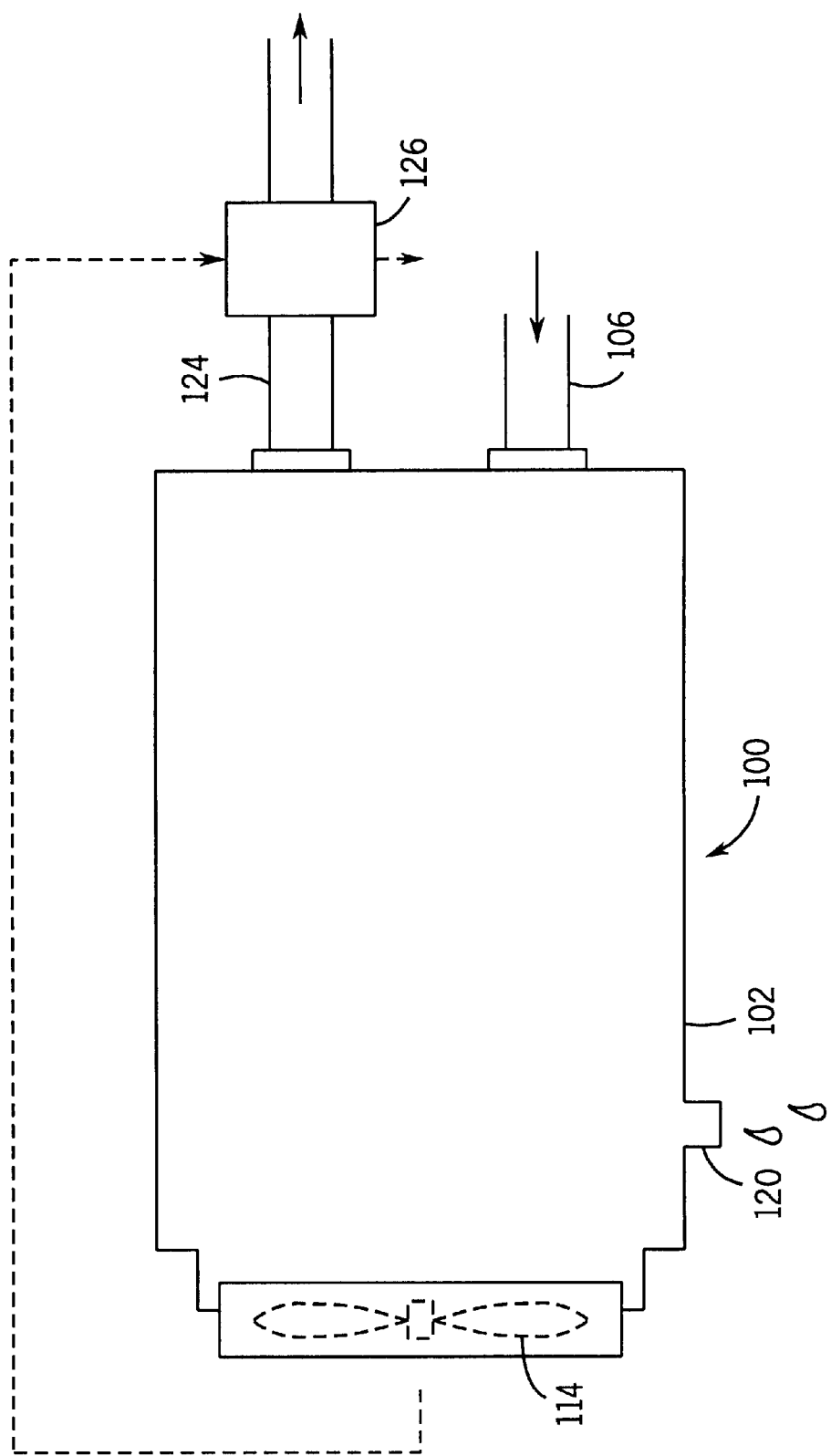
FIG. 2A shows a modification of the dryer shown in FIG. 2.

To facilitate cleaning of dryer 100, thermoelectric element 112 and the associated components may be removed from housing 102, as shown by the dotted line in FIG. 2 for cleaning in a manner similar to that of other mechanical or electric components of the breathing circuit 10 or anaesthesia machine 30. Housing 102 and the associated parts may be autoclaved.

Figure 3:
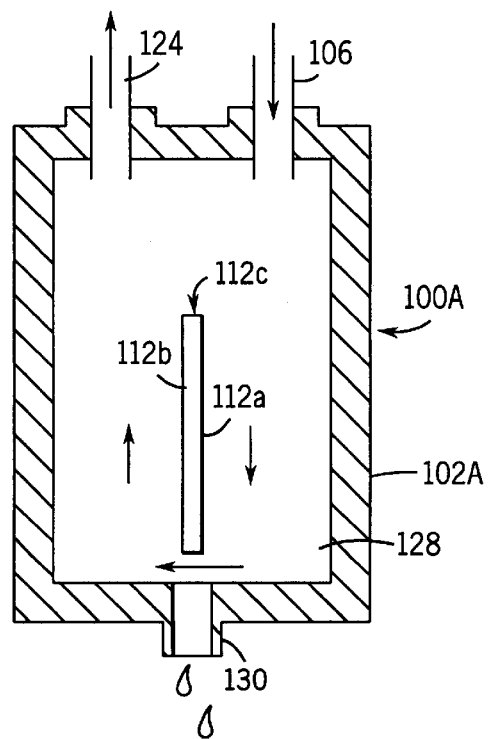
FIG. 3 is a schematic, cross sectional view of a further modification of the dryer.

FIG. 3 shows an alternative embodiment of the dryer as 100A. In FIG. 3, elements similar to those found in FIG. 2 are identified with similar or analogous reference numerals. Housing 102A of dryer 100A forms chamber 128. Chamber 128 contains thermoelectric element 112c. Thermoelectric element 112c is oriented so that the cold surface of the element is adjacent incoming breathing gases from breathing circuit 14 in conduit 106. FIG. 3 shows a vertical orientation for thermoelectric element 112c. The breathing gases are cooled in their passage past the cold surface 112a. The moisture condensed out of the breathing gases by the cooling exits chamber 128 through drain 130. The dried breathing gases are returned to the breathing circuit along the warm surface 112b of thermoelectric element 112c for discharge into conduit 124. Depending on the exact configuration of chamber 128, a greater, lesser, or no amount of heat transfer will occur between the warm breathing gases received in conductor 106 and the dried breathing gases exiting via conduit 124.

The passages in dryer 100/100A are preferably sized to minimize any increase in resistance to breathing gas flow in breathing circuit 14 as a result of the movement of the breathing gases through the dryer.

The rehumidification provided by exchanger 50 in patient limb 22 occurs out of the inspiration limb expiration limb portions of the breathing circuit so that the problem of moisture condensation in these portions of the breathing circuit is not exacerbated. Also, the heat exchange carried out in heat and moisture exchanger 50 provides some reduction in the temperature of the exhaled breathing gases provided to exhalation limb 24, and ultimately to dryer 100/100A, thereby facilitating the cooling and moisture condensation carried out in dryer 100/100A.

FIG. 4 shows an alternative approach to avoiding the accumulation of moisture in breathing circuit 14. In dryer 100b shown in FIG. 4, the breathing gases from $CO_2$ absorber 28 in conduit 106 are passed through a moisture permeable element, such as tube 140. The moisture permeable tube may be formed of the water vapor permeable material made and sold by the Perma Pure, Inc. of New Jersey, USA under the trademark "Nafion." The water vapor in the breathing gases passes through the wall of tubing 140 and is thus removed from the breathing gases. It is deemed preferable to provide turbulent, rather than laminar, flow in tubing 140 to improve the removal of water vapor from the breathing gases. Ridges, several of which are shown as 148, may be provided on the inside of tube 140 for this purpose.

To enhance the removal of moisture, tube 140 may be surrounded along all or a portion of its length by chamber 142. Chamber 142 can be formed as a jacket to surround tube 140. Air is supplied to jacket 142, as for example from a hospital medical air supply, at inlet 144 and removed from the jacket at outlet 146. The air so removed may be discharged to the ambient environment. The air in jacket 142 carries off the moisture passing through the walls of tube 140.

The volume of drying air provided to jacket 142 may be generally the same as the volume of breathing gases passing through tubing 140. However, to reduce the consumption of drying air provided to jacket 142, the supply of drying air can be synchronized with the breathing cycle of subject 12. The supply of air would be provided only during the portion of the breathing cycle in which moist breathing gases in breathing circuit 12 are moving through tube 140. In the configuration shown in FIG. 1, this would be during the inspiration phase of the breathing cycle.

Dryer 100b can be a disposable component of the breathing circuit or can be sterilized as by autoclaving, for reuse.

In designing a breathing circuit including a dyer, it is currently deemed preferable to size the dryer to remove the water vapor released by $CO_2$ absorber 28, as well as any moisture not transferred to the inhaled breathing gases by heat and moisture exchanger 50, i.e. the leakage moisture from heat and moisture exchanger 50. As noted above, approximately 15 mg/liter of moisture is released by $CO_2$ absorber 28. The moisture leakage from heat and moisture exchanger 50 is approximately 7 mg/liter. Heat and moisture exchanger 50 is sized to return the moisture in the exhaled breathing gases to the inhaled breathing gases, except for the moisture leakage amount. In dryer 100b, the water vapor is removed in the drying air in gaseous form. In dryers 100/100A, the water is removed as a liquid, which form may be more convenient for disposal.

It is recognized that other equivalents, alternatives, and modifications aside from those expressly stated, are possible and within the scope of the appended claims.

What is claimed is:

1. An improved breathing circuit for a subject, said breathing circuit comprising:

an inspiration limb providing breathing gases for supply to the subject;

an expiration limb receiving breathing gases containing water vapor from the subject;

means for circulating breathing gases in the breathing circuit to supply breathing gases to the subject and to receive breathing gases from the subject;

a CO2 absorber interposed in said breathing circuit for removing CO2 from the breathing gases provided in said inspiration limb to the subject; and dryer means in said breathing circuit, downstream of said CO2 absorber, for removing water vapor from the breathing gases provided in the inspiration limb to the subject to prevent moisture condensation, said dryer means having means for cooling breathing gases received from said CO2 absorber to remove water vapor therefrom, said dryer means having heat exchanger means for heating cooled breathing gases from which water vapor has been removed and which are provided in said inspiration limb to the subject.

2. The improved breathing circuit according to claim 1 wherein said dryer means includes thermoelectric means for cooling said breathing gases.

3. The improved breathing circuit according to claim 2 wherein said thermoelectric means also produces heat and wherein said heat exchanger means is coupled to said thermoelectric means and employs the heat from said thermoelectric means to heat the cooled breathing gases from which moisture has been removed.

4. The improved breathing circuit according to claim 3 wherein said thermoelectric element has a fan operative associated therewith for improving the cooling action of said thermoelectric element and wherein said heat exchanger means is coupled to an exhaust of said fan for supplying heat removed from said thermoelectric element by said fan to the cooled breathing gases for heating the cooled breathing gases.

5. The improved breathing circuit according to claim 1 wherein said dryer means is sized to remove water vapor released from said $CO_2$ absorber into the breathing gases.

6. The improved breathing circuit according to claim 5 wherein said breathing circuit includes a heat and moisture exchanger in a patient limb for the subject for exchanging heat and moisture from the exhaled breathing gases to the inhaled breathing gases and wherein said heat and moisture exchanger removes a portion of the moisture from the exhaled breathing gases and said dryer means is further defined as sized to remove the remaining portion of the moisture from the breathing gases.

7. The improved breathing circuit according to claim 1 wherein said breathing circuit includes a heat and moisture exchanger in a patient limb for the subject for exchanging heat and moisture from the exhaled breathing gases to the inhaled breathing gases.

8. The improved breathing circuit according to claim 1 further defined as comprising a low-flow anaesthesia breathing circuit.

9. The improved breathing circuit according to claim 1 wherein said heat exchanger means of said dryer means comprises a heat exchanger for heating the cooled breathing gases with breathing gases received from said CO2 absorber.

10. An improved breathing circuit for a subject, said breathing circuit comprising:
   an inspiration limb providing breathing gases for supply to the subject;
   an expiration limb receiving breathing gases containing water vapor from the subject;
   means for circulating breathing gases in the breathing circuit to supply breathing gases to the subject and to receive breathing gases from the subject;
   a CO2 absorber interposed in said breathing circuit for removing CO2 from the breathing gases provided in said inspiration limb to the subject; and
   dryer means in said breathing circuit, downstream of said CO2 absorber, for removing water vapor from the breathing gases provided in the inspiration limb to the subject to prevent moisture condensation, said dryer means comprising a water vapor permeable element having a surface along which the breathing gases received from said CO2 absorber are passed to remove water vapor from the breathing gases.

11. The improved breathing circuit according to claim 10 including means for supplying drying gas to another surface of said water vapor permeable element other than the one along which the breathing gases are passed.

12. The improved breathing circuit according to claim 11 further including means for synchronizing the supply of drying air to said another surface with the breathing cycles of the subject.

13. The improved breathing circuit according to claim 10 wherein said water vapor permeable element comprises a tube formed of water vapor permeable material through which tube the breathing gases pass.

14. The improved breathing circuit according to claim 13 wherein said tube includes means for creating turbulent flow of said breathing gases in said tube.

15. The improved breathing circuit according to claim 13 further including a jacket surrounding said tube along at least a portion of its length for receiving drying gas for removing the water vapor.

16. The improved breathing circuit according to claim 15 further including means for synchronizing the supply of drying air to said jacket with the breathing cycles of the subject.

17. The improved breathing circuit according to claim 10 wherein said dryer is sized to remove water vapor released from said CO2 absorber into the breathing gases.

18. The improved breathing circuit according to claim 17 wherein said breathing circuit includes a heat and moisture exchanger in a patient limb for the subject for exchanging heat and moisture from the exhaled breathing gases to the inhaled breathing gases and wherein said heat and moisture exchanger removes a portion of the moisture from the exhaled breathing gases and said dryer is further defined as sized to remove the remaining portion of the moisture from the breathing gases.

19. The improved breathing circuit according to claim 10 wherein said breathing circuit includes a heat and moisture exchanger in a patient limb for the subject for exchanging heat and moisture from to exhaled breathing gases to the inhaled breathing gases.

20. The improved breathing apparatus according to claim 10 further defined as comprising a low-flow anaesthesia breathing circuit.

21. The improved breathing circuit according to claim 11 further defined as comprising a low-flow anaesthesia breathing circuit.

* * * * *

UNITED STATES PATENT AND TRADEMARK OFFICE
CERTIFICATE OF CORRECTION

PATENT NO.    : 6,523,538 B1
DATED         : February 25, 2003
INVENTOR(S)   : Per Wikefeldt It is certified that error appears in the above-identified patent and that said Letters Patent is hereby corrected as shown below:

Column 6,
Lines 44 and 45, delete "heat exchanger means" and substitute therefor -- heating means downstream of said cooling means --;
Line 52, after the word "said" insert -- dryer means includes thermoelectric means for cooling said breathing gases, wherein said --;
Line 53, delete "means" in the second occurrence;
Line 58, delete "operative" and substitute therefor -- operatively --;
Line 59, delete "improving the cooling action of" and substitute therefor -- removing heat from --;

Column 6,
Line 19, delete "heat exchanger" and substitute therefor -- heating --;

Column 8,
Line 42, delete "11 further defined as comprising a low-flow anesthesia breathing circuit" and substitute therefor -- 1 wherein said heating means of said --;

Signed and Sealed this

Eighth Day of June, 2004

JON W. DUDAS
*Acting Director of the United States Patent and Trademark Office*